(12) United States Patent
Abel et al.

(10) Patent No.: US 11,712,579 B2
(45) Date of Patent: Aug. 1, 2023

(54) RANGE COMPENSATORS FOR RADIATION THERAPY

(71) Applicant: Varian Medical Systems, Inc., Palo Alto, CA (US)

(72) Inventors: Eric Abel, San Jose, CA (US); Corey Zankowski, San Jose, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 218 days.

(21) Appl. No.: 15/656,937

(22) Filed: Jul. 21, 2017

(65) Prior Publication Data
US 2019/0022407 A1 Jan. 24, 2019

(51) Int. Cl.
*A61N 5/10* (2006.01)
*B33Y 50/02* (2015.01)
*B33Y 80/00* (2015.01)

(52) U.S. Cl.
CPC ............ *A61N 5/10* (2013.01); *A61N 5/103* (2013.01); *A61N 5/1077* (2013.01); *B33Y 50/02* (2014.12); *B33Y 80/00* (2014.12); *A61N 2005/1087* (2013.01); *A61N 2005/1096* (2013.01); *A61N 2005/1097* (2013.01)

(58) Field of Classification Search
CPC .. A61N 5/1031; A61N 5/1042; A61N 5/1069; A61N 2005/1087; A61N 2005/1095; A61N 2005/1097; A61N 2005/1096; A61N 5/1077; A61N 5/10; A61N 5/103; B33Y 50/02; B33Y 80/00
See application file for complete search history.

(56) References Cited

U.S. PATENT DOCUMENTS

| | | | |
|---|---|---|---|
| 4,163,901 | A | 8/1979 | Azam |
| 4,914,681 | A | 4/1990 | Klingenbeck et al. |
| 5,153,900 | A | 10/1992 | Nomikos et al. |
| 5,267,294 | A | 11/1993 | Kuroda |
| 5,550,378 | A | 8/1996 | Skillicorn et al. |
| 5,610,967 | A | 3/1997 | Moorman et al. |
| 5,625,663 | A | 4/1997 | Swerdloff et al. |
| 5,682,412 | A | 10/1997 | Skillicorn et al. |
| 5,757,885 | A | 5/1998 | Yao et al. |

(Continued)

FOREIGN PATENT DOCUMENTS

| | | |
|---|---|---|
| CN | 104001270 | 8/2014 |
| CN | 106730407 | 5/2017 |

(Continued)

OTHER PUBLICATIONS

Chang, Sha. "Compensator-intensity-modulated Radiotherapy—A traditional tool for modern application." US Oncological Disease 115 (2006): 1-4 (Year: 2006).*

(Continued)

*Primary Examiner* — Wyatt A Stoffa
(74) *Attorney, Agent, or Firm* — Harness, Dickey & Pierce, P.L.C.

(57) ABSTRACT

A system for treating a patient during radiation therapy includes range compensators. Each of the range compensators shapes a distribution of a dose delivered to the patient by a beam emitted from a nozzle of a radiation treatment system. A positioning component holds the range compensator in place relative to the patient such that the range compensator lies on a path of the beam.

11 Claims, 9 Drawing Sheets

(56) References Cited

U.S. PATENT DOCUMENTS

| | | |
|---|---|---|
| 6,198,802 B1 | 3/2001 | Elliott et al. |
| 6,222,544 B1 | 4/2001 | Tarr et al. |
| 6,234,671 B1 | 5/2001 | Solomon et al. |
| 6,260,005 B1 | 7/2001 | Yang et al. |
| 6,379,380 B1 | 4/2002 | Satz |
| 6,411,675 B1 | 6/2002 | Llacer |
| 6,445,766 B1 | 9/2002 | Whitham |
| 6,504,899 B2 | 1/2003 | Pugachev et al. |
| 6,580,084 B1 | 6/2003 | Hiramoto et al. |
| 6,580,940 B2 | 6/2003 | Gutman |
| 6,888,832 B2 | 5/2005 | Richardson et al. |
| 6,993,112 B2 | 1/2006 | Hesse |
| 7,132,674 B2 * | 11/2006 | Pastyr ..................... G21K 1/04 378/65 |
| 7,268,358 B2 | 9/2007 | Ma et al. |
| 7,423,278 B2 | 9/2008 | Amaldi et al. |
| 7,453,983 B2 | 11/2008 | Schildkraut et al. |
| 7,515,681 B2 | 4/2009 | Ebstein |
| 7,522,706 B2 | 4/2009 | Lu et al. |
| 7,554,275 B2 | 6/2009 | Amaldi |
| 7,560,715 B2 | 7/2009 | Pedroni |
| 7,590,219 B2 | 9/2009 | Maurer, Jr. et al. |
| 7,616,735 B2 | 11/2009 | Maciunas et al. |
| 7,623,623 B2 | 11/2009 | Raanes et al. |
| 7,778,691 B2 | 8/2010 | Zhang et al. |
| 7,807,982 B2 | 10/2010 | Nishiuchi et al. |
| 7,831,289 B2 | 11/2010 | Riker et al. |
| 7,835,492 B1 | 11/2010 | Sahadevan |
| 7,907,699 B2 | 3/2011 | Long et al. |
| 7,984,715 B2 * | 7/2011 | Moyers ................ A61N 5/1049 128/857 |
| 8,071,966 B2 | 12/2011 | Kaiser et al. |
| 8,121,253 B2 | 2/2012 | Nelms |
| 8,253,121 B2 | 8/2012 | Gnutzmann et al. |
| 8,284,898 B2 | 10/2012 | Ho et al. |
| 8,306,184 B2 | 11/2012 | Chang et al. |
| 8,401,148 B2 | 3/2013 | Lu et al. |
| 8,405,056 B2 | 3/2013 | Amaldi et al. |
| 8,406,844 B2 | 3/2013 | Ruchala et al. |
| 8,559,596 B2 | 10/2013 | Thomson et al. |
| 8,600,003 B2 | 12/2013 | Zhou et al. |
| 8,613,694 B2 | 12/2013 | Walsh |
| 8,618,521 B2 | 12/2013 | Loo et al. |
| 8,636,636 B2 | 1/2014 | Shukla et al. |
| 8,644,571 B1 | 2/2014 | Schulte et al. |
| 8,716,663 B2 | 5/2014 | Brusasco et al. |
| 8,798,343 B2 | 8/2014 | Kabus et al. |
| 8,836,332 B2 | 9/2014 | Shvartsman et al. |
| 8,847,179 B2 | 9/2014 | Fujitaka et al. |
| 8,901,519 B2 | 12/2014 | Schardt et al. |
| 8,903,471 B2 | 12/2014 | Heid |
| 8,917,813 B2 | 12/2014 | Maurer, Jr. |
| 8,948,341 B2 | 2/2015 | Beckman |
| 8,958,864 B2 | 2/2015 | Amies et al. |
| 8,983,573 B2 | 3/2015 | Carlone et al. |
| 8,986,186 B2 | 3/2015 | Zhang et al. |
| 8,992,404 B2 | 3/2015 | Graf et al. |
| 8,995,608 B2 | 3/2015 | Zhou et al. |
| 9,018,603 B2 | 4/2015 | Loo et al. |
| 9,033,859 B2 | 5/2015 | Fieres et al. |
| 9,040,945 B1 * | 5/2015 | Hayman ............... A61N 5/1015 378/65 |
| 9,079,027 B2 | 7/2015 | Agano et al. |
| 9,149,656 B2 | 10/2015 | Tanabe |
| 9,155,908 B2 | 10/2015 | Meltsner et al. |
| 9,233,260 B2 | 1/2016 | Slatkin et al. |
| 9,258,876 B2 | 2/2016 | Cheung et al. |
| 9,283,406 B2 | 3/2016 | Prieels |
| 9,308,391 B2 | 4/2016 | Liu et al. |
| 9,330,879 B2 | 5/2016 | Lewellen et al. |
| 9,333,374 B2 | 5/2016 | Iwata |
| 9,468,777 B2 | 10/2016 | Fallone et al. |
| 9,517,358 B2 | 12/2016 | Velthuis et al. |
| 9,526,918 B2 | 12/2016 | Kruip |
| 9,545,444 B2 | 1/2017 | Strober et al. |
| 9,583,302 B2 | 2/2017 | Figueroa Saavedra et al. |
| 9,636,381 B2 | 5/2017 | Basile |
| 9,636,525 B1 | 5/2017 | Sahadevan |
| 9,649,298 B2 | 5/2017 | Djonov et al. |
| 9,656,098 B2 | 5/2017 | Goer |
| 9,694,204 B2 | 7/2017 | Hardemark |
| 9,770,604 B2 * | 9/2017 | Iwata ..................... A61N 5/1044 |
| 9,776,017 B2 * | 10/2017 | Flynn ..................... A61N 5/103 |
| 9,786,054 B2 | 10/2017 | Taguchi et al. |
| 9,786,093 B2 | 10/2017 | Svensson |
| 9,786,465 B2 | 10/2017 | Li et al. |
| 9,795,806 B2 | 10/2017 | Matsuzaki et al. |
| 9,801,594 B2 | 10/2017 | Boyd et al. |
| 9,844,358 B2 | 12/2017 | Wiggers et al. |
| 9,854,662 B2 | 12/2017 | Mishin |
| 9,884,206 B2 | 2/2018 | Schulte et al. |
| 9,931,522 B2 | 4/2018 | Bharadwaj et al. |
| 9,962,562 B2 | 5/2018 | Fahrig et al. |
| 9,974,977 B2 | 5/2018 | Lachaine et al. |
| 9,987,502 B1 | 6/2018 | Gattiker et al. |
| 10,007,961 B2 | 6/2018 | Grudzinski et al. |
| 10,022,564 B2 | 7/2018 | Thieme et al. |
| 10,071,264 B2 | 9/2018 | Liger |
| 10,080,912 B2 | 9/2018 | Kwak et al. |
| 10,092,774 B1 | 10/2018 | Vanderstraten et al. |
| 10,183,179 B1 | 1/2019 | Smith et al. |
| 10,188,875 B2 | 1/2019 | Kwak et al. |
| 10,206,871 B2 | 2/2019 | Lin et al. |
| 10,212,800 B2 | 2/2019 | Agustsson et al. |
| 10,232,193 B2 | 3/2019 | Iseki |
| 10,258,810 B2 | 4/2019 | Zwart et al. |
| 10,272,264 B2 | 4/2019 | Ollila et al. |
| 10,279,196 B2 | 5/2019 | West et al. |
| 10,293,184 B2 | 5/2019 | Pishdad et al. |
| 10,307,614 B2 | 6/2019 | Schnarr |
| 10,307,615 B2 | 6/2019 | Ollila et al. |
| 10,315,047 B2 | 6/2019 | Glimelius et al. |
| 10,413,755 B1 | 9/2019 | Sahadevan |
| 10,449,389 B2 | 10/2019 | Ollila et al. |
| 10,485,988 B2 | 11/2019 | Kuusela et al. |
| 10,507,338 B2 * | 12/2019 | Kuwahara ........... A61N 5/1049 |
| 10,525,285 B1 | 1/2020 | Friedman |
| 10,549,117 B2 | 2/2020 | Vanderstraten et al. |
| 10,603,514 B2 | 3/2020 | Grittani et al. |
| 10,609,806 B2 | 3/2020 | Roecken et al. |
| 10,636,609 B1 | 4/2020 | Bertsche et al. |
| 10,660,588 B2 | 5/2020 | Boyd et al. |
| 10,661,100 B2 | 5/2020 | Shen |
| 10,682,528 B2 | 6/2020 | Ansorge et al. |
| 10,702,716 B2 | 7/2020 | Heese |
| 10,758,746 B2 | 9/2020 | Kwak et al. |
| 10,870,018 B2 | 12/2020 | Bartkoski et al. |
| 2002/0000118 A1 | 1/2002 | Panizzolo |
| 2002/0030164 A1 * | 3/2002 | Akiyama .................. G21K 5/04 250/492.1 |
| 2004/0098445 A1 * | 5/2004 | Baumann ............... H04L 69/329 709/200 |
| 2004/0183035 A1 * | 9/2004 | Yanagisawa ............. A61N 5/10 250/492.3 |
| 2005/0167616 A1 * | 8/2005 | Yanagisawa ............. G21K 1/10 250/492.1 |
| 2007/0287878 A1 | 12/2007 | Fantini et al. |
| 2008/0023644 A1 | 1/2008 | Pedroni |
| 2008/0049897 A1 | 2/2008 | Molloy |
| 2009/0063110 A1 | 3/2009 | Failla et al. |
| 2009/0287467 A1 | 11/2009 | Sparks et al. |
| 2010/0070236 A1 * | 3/2010 | Campana ................. A61N 5/10 523/105 |
| 2010/0119032 A1 | 5/2010 | Yan et al. |
| 2010/0177870 A1 | 7/2010 | Nord et al. |
| 2010/0178245 A1 | 7/2010 | Arnsdorf et al. |
| 2010/0195793 A1 * | 8/2010 | Nelms ................... A61N 5/1042 378/65 |
| 2010/0260317 A1 | 10/2010 | Chang et al. |
| 2010/0288945 A1 * | 11/2010 | Gnutzmann ............. G21K 1/10 250/503.1 |
| 2010/0303205 A1 * | 12/2010 | Kapoor ............... G06Q 10/0633 378/65 |

(56) References Cited

U.S. PATENT DOCUMENTS

| | | | |
|---|---|---|---|
| 2011/0006214 A1 | 1/2011 | Marc-Oliver | |
| 2011/0006224 A1 | 1/2011 | Maltz et al. | |
| 2011/0046694 A1* | 2/2011 | Forsell | A61N 5/0613 |
| | | | 607/45 |
| 2011/0091015 A1 | 4/2011 | Yu et al. | |
| 2011/0135058 A1 | 6/2011 | Sgouros et al. | |
| 2012/0076271 A1 | 3/2012 | Yan et al. | |
| 2012/0157746 A1 | 6/2012 | Meltsner et al. | |
| 2012/0171745 A1 | 7/2012 | Itoh | |
| 2012/0197058 A1* | 8/2012 | Shukla | A61N 5/1047 |
| | | | 600/1 |
| 2012/0253495 A1* | 10/2012 | Wright | A61N 5/103 |
| | | | 700/98 |
| 2013/0087721 A1* | 4/2013 | Nishio | A61N 5/1042 |
| | | | 703/1 |
| 2013/0116929 A1 | 5/2013 | Carlton et al. | |
| 2013/0150922 A1 | 6/2013 | Butson et al. | |
| 2013/0177641 A1 | 7/2013 | Ghoroghchian | |
| 2013/0231516 A1 | 9/2013 | Loo et al. | |
| 2013/0253252 A1* | 9/2013 | Iwata | A61N 5/10 |
| | | | 600/1 |
| 2014/0177807 A1 | 6/2014 | Lewellen et al. | |
| 2014/0185776 A1 | 7/2014 | Li et al. | |
| 2014/0206926 A1 | 7/2014 | van der Laarse | |
| 2014/0275706 A1 | 9/2014 | Dean et al. | |
| 2014/0369476 A1 | 12/2014 | Harding | |
| 2015/0011817 A1 | 1/2015 | Feng | |
| 2015/0057484 A1 | 2/2015 | Amaldi | |
| 2015/0094838 A1* | 4/2015 | Mac Laverty | G06F 30/00 |
| | | | 700/98 |
| 2015/0202464 A1 | 7/2015 | Brand et al. | |
| 2015/0306423 A1 | 10/2015 | Bharat et al. | |
| 2016/0193482 A1 | 7/2016 | Fahrig et al. | |
| 2016/0256709 A1* | 9/2016 | Robar | G16H 50/30 |
| 2016/0279444 A1 | 9/2016 | Schlosser | |
| 2016/0310764 A1 | 10/2016 | Bharadwaj et al. | |
| 2017/0128739 A1* | 5/2017 | Dilmanian | A61N 5/1084 |
| 2017/0173363 A1* | 6/2017 | Wang | A61N 5/1048 |
| 2017/0189721 A1 | 7/2017 | Sumanaweera et al. | |
| 2017/0203129 A1 | 7/2017 | Dessy | |
| 2017/0281973 A1 | 10/2017 | Allen et al. | |
| 2017/0364062 A1* | 12/2017 | Ju | A61N 5/1031 |
| 2017/0368370 A1* | 12/2017 | Tallhamer | G06T 7/521 |
| 2018/0008841 A1* | 1/2018 | Iwata | A61N 5/1081 |
| 2018/0021594 A1 | 1/2018 | Papp et al. | |
| 2018/0043183 A1 | 2/2018 | Sheng et al. | |
| 2018/0056090 A1 | 3/2018 | Jordan et al. | |
| 2018/0099154 A1 | 4/2018 | Prieels | |
| 2018/0099155 A1 | 4/2018 | Prieels et al. | |
| 2018/0099159 A1 | 4/2018 | Forton et al. | |
| 2018/0154183 A1 | 6/2018 | Sahadevan | |
| 2018/0197303 A1 | 7/2018 | Jordan et al. | |
| 2018/0207425 A1 | 7/2018 | Carlton et al. | |
| 2018/0235554 A1* | 8/2018 | Burgett | A61B 6/08 |
| 2018/0236268 A1 | 8/2018 | Zwart et al. | |
| 2018/0242931 A1* | 8/2018 | Holman | A61C 9/0053 |
| 2019/0022407 A1 | 1/2019 | Abel et al. | |
| 2019/0022422 A1 | 1/2019 | Trail et al. | |
| 2019/0022423 A1* | 1/2019 | Dilmanian | A61B 6/06 |
| 2019/0054315 A1 | 2/2019 | Isola et al. | |
| 2019/0070435 A1 | 3/2019 | Joe Anto et al. | |
| 2019/0091488 A1* | 3/2019 | Ding | A61N 5/1043 |
| 2019/0168027 A1 | 6/2019 | Smith et al. | |
| 2019/0255361 A1 | 8/2019 | Mansfield | |
| 2019/0282832 A1* | 9/2019 | Robar | G16H 50/30 |
| 2019/0299027 A1 | 10/2019 | Fujii et al. | |
| 2019/0299029 A1 | 10/2019 | Inoue | |
| 2019/0311878 A1* | 10/2019 | Mizushima | H01J 37/3005 |
| 2019/0351259 A1 | 11/2019 | Lee et al. | |
| 2020/0001118 A1 | 1/2020 | Snider, III et al. | |
| 2020/0022248 A1 | 1/2020 | Yi et al. | |
| 2020/0030633 A1 | 1/2020 | Van Heteren et al. | |
| 2020/0035438 A1 | 1/2020 | Star-Lack et al. | |
| 2020/0069818 A1 | 3/2020 | Jaskula-Ranga et al. | |
| 2020/0164224 A1 | 5/2020 | Vanderstraten et al. | |
| 2020/0178890 A1 | 6/2020 | Otto | |
| 2020/0197730 A1 | 6/2020 | Safavi-Naeini et al. | |
| 2020/0254279 A1 | 8/2020 | Ohishi | |
| 2020/0269068 A1 | 8/2020 | Abel et al. | |
| 2020/0276456 A1 | 9/2020 | Swerdloff | |
| 2020/0282234 A1 | 9/2020 | Folkerts et al. | |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 2108401 | 10/2009 |
| EP | 2810693 | 12/2014 |
| EP | 3043863 A1 | 7/2016 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 2014161706 A | 9/2014 |
| JP | 2017098000 A | 6/2017 |
| JP | 2019097969 | 6/2019 |
| WO | 2007017177 | 2/2007 |
| WO | 2010018476 | 2/2010 |
| WO | WO2010088442 | 8/2010 |
| WO | WO2012135196 | 10/2012 |
| WO | 2013081218 | 6/2013 |
| WO | 2013133936 | 9/2013 |
| WO | 2014139493 | 9/2014 |
| WO | 2015038832 | 3/2015 |
| WO | WO2015077881 | 6/2015 |
| WO | 2015102680 | 7/2015 |
| WO | WO2015153746 | 10/2015 |
| WO | 2016122957 | 8/2016 |
| WO | 2017156316 | 9/2017 |
| WO | 2017173443 | 10/2017 |
| WO | 2017174643 | 10/2017 |
| WO | 2018137772 | 8/2018 |
| WO | 2018152302 | 8/2018 |
| WO | 2019018341 A1 | 1/2019 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

Favaudon, Vincent, et al. "Ultrahigh dose-rate FLASH irradiation increases the differential response between normal and tumor tissue in mice." Science translational medicine 6.245 (2014): 245ra93-245ra93 (Year: 2014).*

Wen C. His, Michael F. Moyers, Dmitri Nichporov, Vladimir Anferov, Mark Wolanski, Chris E. Allgower, Jonathan B. Farr, Anthony E. Mascia, Andreis N. Schreuder, "Energy spectrum control for modulated proton beams", Medical Physics, (2009) 36(6) 2297-2308, http://www.ncbi.nlm.nih.gov/pmc/articles/PMC2832068/.

V. Anferov, M. Ball, G.P. Berg, B. Broderick, J. Collins, G. East, D. Friesel, D. Jenner, W.P. Jones, J. Katuin, S. Klein, C. Nelson, N. Schreuder, Wm. Starks, J. Self, "The Indiana University Midwest Proton Radiation Institute", Proceedings of the 2001 Particle Accelerator Conference, (2001) p. 645-64 https://accelconf.web.cern.ch/accelconf/p01/PAPERS/FOAA004.PDF.

Th. Haberer,W. Becher,D. Schardt,G. Kraft "Magnetic scanning system for heavy ion therapy" Nuclear Instruments and Methods in

(56) References Cited

OTHER PUBLICATIONS

Physics Research Section A: Accelerators, Spectrometers, Detectors and Associated Equipment , NIM , Elsevie, Jun. 10, 1993, vol. 330, Issues 1-2, Jun. 10, 1993, pp. 296-305.
Amaldi, Tera Foundation, Novara, Italy A. Degiovanni, CERN, Geneva, Switzerland Linac 2014. Proton and Carbon Linacs for Hadron Therapy U. http://accelconf.web.cern.ch/AccelConf/LINAC2014/papers/friob02.pdf.
Montay-Gruel P, Petersson K, Jaccard M, Boivin G, Germond JF, Petit B, Doenlen R, Favaudon V, Bochud F, Bailat C, Bourhis J, Vozenin MC. Irradiation in a flash: Unique sparing of memory in mice after whole brain irradiation with dose rates above 100Gy/s. Radiother Oncol. May 22, 2017. pii: 30167-8140(17)30365-1. doi: 10.1016/j.radonc.2017 05.003. [Epub ahead of print] PubMed PMID: 28545957.
Favaudon V, Caplier L, Monceau V, Pouzoulet F, Sayarath M, Fouillade C, Poupon MF, Brito I, Hupe P, Bourhis J, Hall J, Fontaine JJ, Vozenin MC. Ultrahigh dose-rate FLASH irradiation increases the differential response between normal and tumor tissue in mice. Sci Transl Med. Jul. 16, 2014;6(245):245ra93. doi: 10.1126/scitranslmed.3008973. PubMed PMID: 25031268.
Loo BW, Schuler E, Lartey FM, Rafat M, King GJ, Trovati S, Koong AC, Maxim PG. Delivery of Ultra-Rapid Flash Radiation Therapy and Demonstration of Normal Tissue Sparing After Abdominal Irradiation of Mice. International Journal of Radiation Oncology Biology Physics. vol. 98 Issue: 2 pp. E16-E16 Supplement: S Meeting Abstract: P003 Published: Jun. 1, 2017.
M. Bopp, H. Fitze, P. Sigg, and L. Stingelin "Upgrade concepts of the PSI accelerator RF systems for a projected 3 mA operation", Citation: AIP Conference Proceedings 600, 300 (2001); doi: 10.1063/1.1435259.
S. Benedetti, A. Grudiev, and A. Latina Phys. Rev. Accel. Beams 20, 040101—Published Apr. 13, 2017.
Z. Li, et al., Normal conducting cw transverse crab cavity for producing short pulses in spear3, Proceedings of IPAC2017, Copenhagen, Denmark.
Valery Dolgashev, Sami Tantawi, Yasuo Higashi, Bruno Spataro, "Geometric dependence of radio-frequency breakdown in normal conducting accelerating structures," Applied Physics Letters, vol. 97, Issue 17, p. 171501 -171501-3, Oct. 2010.
Lisa Laurent, Sami Tantawi, Valery Dolgashev, Chris Nantista, Yasuo Higashi, Markus Aicheler, Samuli Heikkinen, and Walter Wuensch, Experimental Study of RF Pulsed Heating Phys. Rev. ST Accel. Beams 14, 041001 (2011) [21 pages].
S. Tantawi, Z. Li, patent pending, Title: "Distributed Coupling and Multi-Frequency Microwave Accelerators", Filed Jul. 9, 2014, U.S. Appl. No. 62/022,469.
S.Tantawi, M.Nasr, "Designs and High Power Tests of Distributed Coupling Linacs" IFIC, Jun. 13-16, 2017 , Valencia , Spainhttps://indico.cem.ch/event/589548/contributions/2615455/attachments/1479738/2294080/Mamdouh_High_Gradient_2017.pdf.
Jensen, Aaron, Jeff Neilson, and Sami Tantawi. "X-band multi-beam klystron design and progress report." Vacuum Electronics Conference (IVEC), 2015 IEEE International. IEEE, 2015.
K.Halbach, "Design of permanent multipole magnets with oriented rare earth cobalt material", Nuclear Instruments and Methods , vol. 169, Issue 1, Feb. 1, 1980, pp. 1-10 [http://www.sciencedirect.com/science/article/pii/0029554X80900944].
J. K. Lim, P. Frigola, G. Travish, J. B. Rosenzweig, S. G. Anderson, W. J. Brown, J. S. Jacob, C. L. Robbins, and A. M. Tremaine, "Adjustable, short focal length permanent-magnet quadrupole based electron beam final focus system" Phys. Rev. ST Accel. Beams 8, 072401—Published Jul. 15, 2005.
Sayyed Bijan Jiaa, Mohammad Hadi Hadizadeha, Ali Asghar Mowlavi ,Mahdy Ebrahimi Loushab "Evaluation of energy deposition and secondary particle production in proton therapy of brain using a slab head phantom" Elsevier, Reports of Practical Oncology & Radiotherapy, vol. 19, Issue 6, Nov.-Dec. 2014, pp. 376-384.
J.Perl, J Shin, J Schümann, B Faddegon and H Paganetti, "TOPAS—An innovative proton Monte Carlo platform for research and clinical applications," Med. Phys. 39:6818-6837, 2012, PMID: 23127075, PMID: 23127075.
Lisa Polster, Jan Schuemann, Ilaria Rinaldi, Lucas Burigo, Aimee Louise McNamara, Robert D Stewart, Andrea Attili, David J. Carlson, Alejandro Carabe-Femadez, Bruce Faddegon, Joseph Perl, and Harald Paganetti, "Extension of TOPAS for the simulation of proton radiation on molecular and cellular endpoints," Phys Med Biol. Jun. 10, 2015;60 (13):5053-5070, PMID: 26061583.
Qiyong Fan, Akshay Nanduri, Samuel Mazin, Lei Zhu, "Emission guided radiation therapy for lung and prostate cancers: A feasibility study on a digital patient", Med. Phys. 39 (11), Nov. 2012, 0094-2405/2012/39 (11)/7140/13, 13 pages.
Vincent Favuadon, Laura Caplier, Virginie Monceau, Frederic Pouzoulet, Mano Sayarath, Charles Fouillade, Marie-France Poupon, Isabel Brito, Philippe Hupe, Jean Bounhis,Janet Hall, Jean-Jacques Fontaine, Marie-Catherine Vozenin, vol. 6 Issue 245 245ra93, www.ScienceTranslationalMedicine.org, UltraHigh dose-rate FLASH irradiation increase4s the differential response between normal and tumor tissue in mice, 9 pages, 2015.
Radiotherapy "flashes" to reduce side effects, An effect for each mode of adminislialion, Images of tissue sections, Ultra-high dose-rate, Science Translational Medicine, Jul. 16, 2014, 3 pages.
To introduce the concept of pseudo beam's-eye-view (pBEV), to establish a framework for computer-assisted beam orientation selection in intensity-modulated radiation therapy(IMRT), and to evaluate the utility of the proposed techniquie, Dec. 1, 2001 vol. 51, Issue 5, 3 pages, Pseudo beam's-eye-view as applied to beam orientation selection in intensity-modulated radiation therapy.
M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/S41598-020-65819-y.
Brahim Oraiqat et al., "An Ionizing Radiation Acoustic Imaging (iRAI) Technique for Real-Time Dosimetric Measurements for FLASH Radiotherapy," Medical Physics, vol. 47, Issue10, Oct. 2020, pp. 5090-5101, First published: Jun. 27, 2020, https://doi.org/10.1002/mp.14358.
K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5lbHNIdmllci5jb20vY29udGVudC9hcnRpY2xlL3BpaS9zMDE2NzgxNDAxNjMwMTcyNA==pdf.
Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.
Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.
Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nim.nih.gov/pmc/articles/PMC3505203/ doi: 10.1118/1.4761951.
Favaudon et al., "Ultrahigh dose-rate, "flash" irradiation minimizes the side-effects of radiotherapy," Cancer/Radiotherapy, vol. 19, Issues 6-7 , Oct. 2015 , pp. 526-531, Available online Aug. 12, 2015, https://doi.org/10.1016/j.canrad.2015.04.006.
O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.
Bjorn Zackrisson, "Biological Effects Of High Energy Radiation And Ultra High Dose Rates," Umea University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

(56) References Cited

OTHER PUBLICATIONS

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, p. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, P1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al., "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for eady and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng-pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J. Groen, "FLASH optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019. https://www.ncbi.nlm.nih.gov/pmc/articles/PMC5904040/Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

(56) References Cited

OTHER PUBLICATIONS

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS ONE, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, trttps://www.itnonline.com/content/netherlands-proton-therapy-center-delivers-first-clinical-flash-irradiation.

R. M. De Kruijff, "Flash radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus On The Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/ Published in final edited form as: Radiat Res. Jan. 2020; 193(1): 1-4. Published online Oct. 28, 2019. doi: 10.1667/RR15537.1.

Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate FLASH radiotherapy to minimize the complications of radiotherapy," 2014, https://siric.curie.fr/sites/default/files/atoms/files/flashrad.pdf.

Tami Freeman, "FLASH radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

Intraop Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A Flash back to radiotherapy's past and then fast forward to the future," J Cancer Prev Curr Res. 2019;10(6):142-144. published Nov. 13, 2019, DOI: 10.15406/jcpcr.2019.10.00407.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: Flash: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement, S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.

Oncolink Team, "Radiation Therapy: Which type is right for me?", OncoLink Penn Medicine, last reviewed Mar. 3, 2020, Trustees of

(56) References Cited

OTHER PUBLICATIONS the University of Pennsylvania, https://www.oncolink.org/cancer-treatment/radiation/introduction-to-radiation-therapy/radiation-therapy-which-type-is-right-for-me.

Marco Durante et al., "Faster and safer? FLASH ultra-high dose rate in radiotherapy," Br J Radiol 2018; 91(1082): Jun. 28, 2017, British Institute of Radiology, Published Online: Dec. 15, 2017, https://doi.org/10.1259/bjr.20170628.

John R. Fischer, "PMB launches FLASH radiotherapy system for use in clinical trials," Healthcare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432.CCR-17-3375.full.pdf.

Bragg Peak. Massachusetts General Hospital, Physics Division, retrieved from https://gray.mgh.harvard.edu/attachments/article/337/Techniques%20of%20Proton%20Radiotherapy%20(10)%20Bragg%20Peak.pdf (Year: 2021).

https://brilliant.org/wiki/irregular-polygons/, downloaded Mar. 24, 2022 (year: 2022).

https://en.wikipedia.org/wiki/List_of_regular_polytopes_and_compounds, downloaded Mar. 24, 2022 (year: 2022).

Park J. W., and J. W. Yea. "Three-dimensional customized bolus for intensity-modulated radio in a patient with Kimura's disease involving the auricle." Cancer/zRadiotherapie 20.3 (2016): 205-209 (Year: 2016).

https://en.wikipedia.org/wiki/Regular_polyhedron, downloaded Mar. 24, 2022 (year: 2022).

\* cited by examiner

RANGE COMPENSATORS FOR RADIATION THERAPY

BACKGROUND

The use of radiation therapy to treat cancer is well known. Typically, radiation therapy involves directing a high energy beam of radiation into a target (e.g., a tumor or lesion) in a patient.

A radiation therapy device typically includes, among other components, a platform (e.g., a table or couch) to support the patient and a nozzle that emits the radiation beam. The patient is in a supine position, for example, and the nozzle directs the beam into the target (e.g., the tumor being treated).

During treatment, it is important to keep the patient as stationary (immobilized) as possible, so that the beam remains pointed at the target and at the proper place within the target. Otherwise, the radiation beam may miss parts of the target or might land on normal (healthy) tissue outside the target. Fixation or immobilization devices are used to secure a patient's position and keep the patient stationary during radiotherapy.

A standard treatment process includes scanning and imaging the patient prior to treatment to detect internal organs and locate the target (e.g., the tumor). Immobilization devices customized for the patient are designed and a treatment plan is generated. The designs for the immobilization devices are sent to a manufacturer. The manufactured immobilization devices are delivered to the treatment center, where they are tested prior to beginning radiotherapy. If changes are needed, then the process of interacting with the manufacturer is repeated. The patient then returns and treatment can begin.

The conventional approach described above is problematic for a variety of reasons. First, multiple patient visits are required—at least one visit is required prior to treatment in order to design the immobilization devices. Also, the need to involve a manufacturer increases costs. Furthermore, time may be lost while the immobilization devices are shipped from and perhaps back to the manufacturer.

Also during treatment, the nozzle and/or the patient are typically moved relative to one another so that the beam can be directed into the target from different directions/angles (beam geometries). The target may have an irregular shape and/or the amount (depth) of normal, healthy tissue on the beam path may vary depending on the beam geometry. In general, it may be necessary to shape the dose distribution delivered by a beam according to the shape and depth of the target and the beam geometry.

A range compensator is used to change (e.g., decrease) the energies of particles in a beam to affect the distance that the beam penetrate into the target. The range compensator may be located downstream of the particle accelerator before the nozzle or in the nozzle itself.

A recent radiobiology study has demonstrated the effectiveness of delivering an entire, relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time. In general, because of the higher dose rates associated with FLASH RT, it is desirable to minimize the amount of time that normal, healthy tissue outside the target is irradiated. A means of achieving that is to produce a radiation treatment plan in which beams do not overlap, or overlap as little as possible, outside the target. With FLASH RT, the direction/angle of the nozzle is set so that the nozzle is aimed at the target; the range compensator is adjusted to account for the beam energy, the distance to the target, and the shape of the target (the distance across the target); and then the beam is turned on and quickly turned off. The process is repeated for the next beam geometry. To reduce overall treatment time for the comfort of the patient, it is desirable to be able quickly adjust the range compensator for the different beam geometries.

SUMMARY

In embodiments, an immobilization device for limiting movement of a patient on a patient support device during radiation therapy includes a range compensator and a positioning component. The range compensator shapes a distribution of a dose delivered to a patient by an incident beam emitted from a nozzle of a radiation treatment system. The dose distribution may be relatively uniform across the target, or it may be non-uniform (e.g., the distribution may include a Bragg peak). The positioning component holds the immobilization device in place relative to the patient. In effect, in one or more such embodiments, the range compensator is moved from the nozzle of a radiation treatment system to the immobilization device. This multi-functional aspect of the immobilization device can improve radiation treatments and reduce costs.

The immobilization device can be fabricated using a three-dimensional printer. Accordingly, patient-specific devices can be readily, quickly, inexpensively, and effectively produced on-site without an external manufacturer, avoiding shipping from and perhaps back to the manufacturer. The number of patient visits can be reduced because, for example, the immobilization device can be fabricated when the patient arrives for a treatment and/or because the immobilization device can be quickly modified on-site after testing for fit and/or function or while the radiation therapy is being performed. Furthermore, the immobilization devices can be recycled and do not need to be stored, which contributes to the cost savings.

In embodiments, a system for treating a patient during radiation therapy includes multiple range compensators. In practice, each range compensator is located on the patient. At least one positioning component holds the range compensators in place relative to the patient such that each range compensator lies on a path of a beam emitted from a nozzle of a radiation treatment system. In embodiments, at least one of the range compensators is part of an immobilization device such as the aforementioned immobilization device. Each of the range compensators shapes a distribution of a dose delivered to the patient by the beam. The dose distribution may be relatively uniform across the target, or it may be non-uniform (e.g., the distribution may include a Bragg peak). In effect, in embodiments, the range compensator is moved from the beam delivery system (e.g., from the nozzle) of a radiation treatment system to a location on the patient.

In another embodiment, a computer-implemented method of radiation treatment planning includes accessing, from a memory of the computer, parameters for a radiation treatment plan. The parameters include, for example, the number of beams and paths of the beams relative to a position of a patient on a patient support device. Locations on the patient for range compensators are identified. Specifically, each range compensator is located on the patient so that each range compensator lies on at least one of the beam paths.

In another embodiment, a computer-implemented radiation treatment method includes accessing, from a memory of the computer, a radiation treatment plan that prescribes a distribution of a dose to be delivered to a target in a patient by a number of beams emitted from a nozzle of a radiation treatment system. The nozzle is controlled to aim the beams at range compensators positioned at different locations on the patient. The nozzle is aimed at a first range compensator, and then a first beam is turned on and emitted at the first range compensator. The first beam is then turned off, the nozzle is aimed at a second range compensator, and a second beam is turned on and emitted at the second range compensator. This process can be repeated for each of the number of beams.

Range compensators in embodiments according to the invention can be used to shape dose distribution in the target in lieu of, but also in combination with, a conventional range compensator. By strategically locating the range compensators on the patient, different beam geometries are readily accommodated. It is not necessary to wait until a range compensator is adjusted when the beam geometry changes; instead, a properly configured range compensator is already in place. Thus, radiation therapy can be quickly performed, thereby facilitating patient comfort. Range compensators in embodiments according to the invention also can be used to provide the prescribed dose inside the target and thus can facilitate radiation treatment planning using FLASH RT by making it easier to address that aspect of the planning.

These and other objects and advantages of embodiments according to the present invention will be recognized by one skilled in the art after having read the following detailed description, which are illustrated in the various drawing figures.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Figure 1:
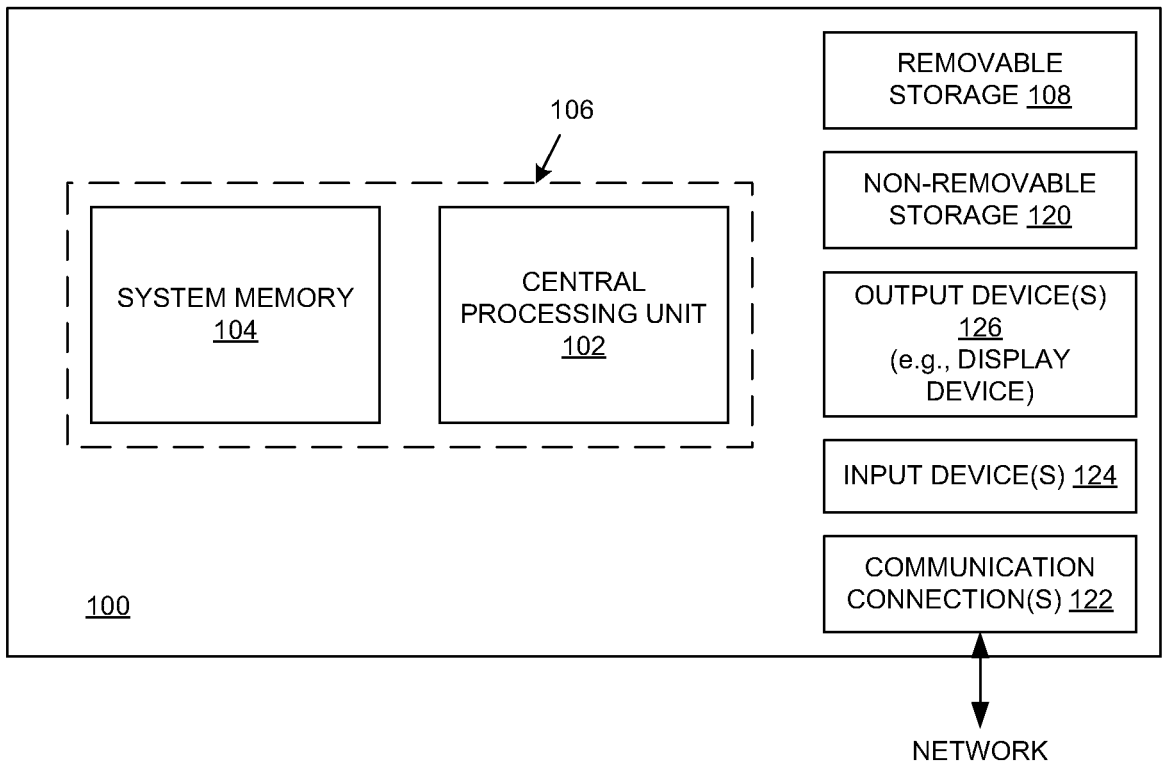
FIG. 1 shows a block diagram of an example of a computing system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "controlling," "identifying," "aiming," "turning on," "turning off," or the like, refer to actions and processes (e.g., the flowcharts of FIGS. 6, 7, 9, and 10) of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices. Terms such as "dose" or "energy" generally refer to a dose or energy value; the use of such terms will be clear from the context of the surrounding discussion.

Portions of the detailed description that follows are presented and discussed in terms of a method. Although steps and sequencing thereof are disclosed in figures herein (e.g., FIGS. 6, 7, 9, and 10) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computing system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like. Depending on how it is to be used, the system 100—by executing the appropriate instructions or the like—can be used to implement a planning system used to create immobilization devices using a three-dimensional (3D) printer, as a control system to implement a radiation treatment plan in a radiation treatment system, or to implement a system for radiation treatment planning.

Figure 2:
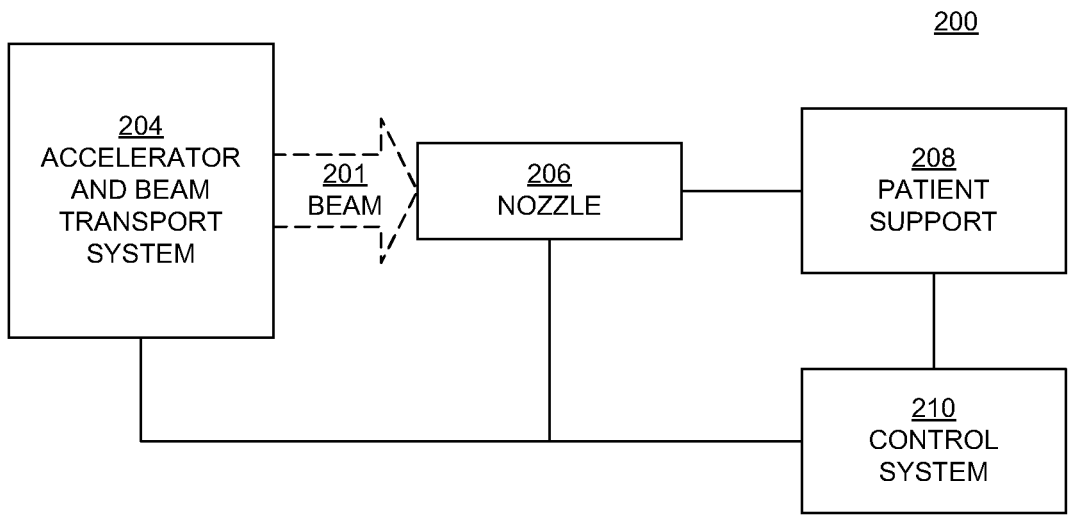
FIG. 2 is a block diagram showing selected components of a radiation treatment system upon which embodiments according to the present invention can be implemented.

FIG. 2 is a block diagram showing selected components of a radiation treatment system 200 upon which embodiments according to the present invention can be implemented. In the example of FIG. 2, the system 200 includes an accelerator and beam transport system 204 that generates and/or accelerates a beam 201. Embodiments according to the invention can generate and deliver proton beams, electron beams, neutron beams, photon beams, ion beams, or atomic nuclei beams (e.g., using elements such as carbon, helium, or lithium). The operations and parameters of the accelerator and beam transport system 204 are controlled so that the intensity, energy, size, and/or shape of the beam are dynamically modulated or controlled during treatment of a patient according to a radiation treatment plan.

A recent radiobiology study has demonstrated the effectiveness of delivering an entire, relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time. For FLASH RT, the accelerator and beam transport system 204 can generate beams that can deliver at least four (4) grays (Gy) in less than one second, and may deliver as much as 20 Gy or 50 Gy or more in less than one second.

The nozzle 206 is used to aim the beam toward various locations (a target) within a patient supported on the patient support device 208 (e.g., a chair, couch, or table) in a treatment room. A target may be an organ, a portion of an organ (e.g., a volume or region within the organ), a tumor, diseased tissue, or a patient outline.

The nozzle 206 may be mounted on or may be a part of a gantry (FIG. 3) that can be moved relative to the patient support device 208, which may also be moveable. In embodiments, the accelerator and beam transport system 204 is also mounted on or is a part of the gantry; in another embodiment, the accelerator and beam transport system is separate from (but in communication with) the gantry.

The control system 210 of FIG. 2 receives and implements a prescribed treatment plan. In embodiments, the control system 210 includes a computing system having a processor, memory, an input device (e.g., a keyboard), and perhaps a display; the system 100 of FIG. 1 is an example of a platform for the control system 210. The control system 210 can receive data regarding operation of the system 200. The control system 210 can control parameters of the accelerator and beam transport system 204, nozzle 206, and patient support device 208, including parameters such as the energy, intensity, size, and/or shape of the beam, direction of the nozzle, and position of the patient support device (and the patient) relative to the nozzle, according to data the control system 210 receives and according to the radiation treatment plan.

Immobilization Device Including Range Compensator for Radiation Therapy

Figure 3:
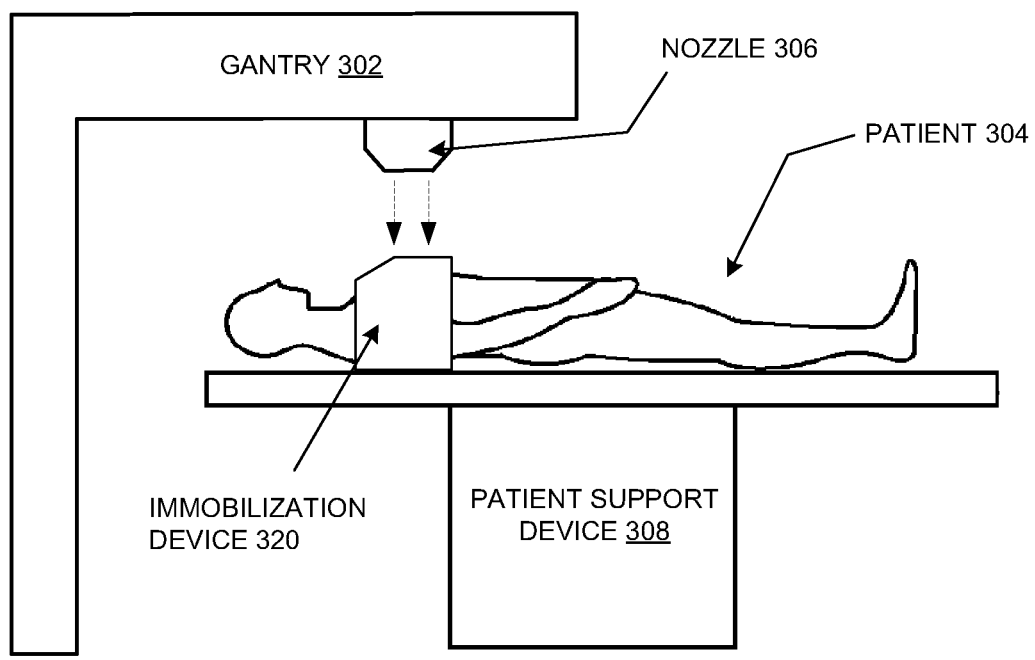
FIG. 3 illustrates elements of a radiation treatment system in embodiments according to the invention.

FIG. 3 illustrates elements of a radiation treatment system 300 for treating a patient 304 in embodiments according to the invention. The system 300 is an example of an implementation of the radiation treatment system 200 of FIG. 2, for example. In embodiments, the gantry 302 and nozzle 306 can be moved up and down the length of the patient 304 and/or around the patient, and the gantry and nozzle can move independently of one another. In embodiments, the patient support device 308 can be moved to different positions relative to the gantry 302 and nozzle 306, rotated about its longitudinal axis, rotated about a central (normal) axis, and/or tilted back and forth about a transverse axis. While the patient 304 is supine in the example of FIG. 3, the invention is not so limited. For example, the patient 304 can instead be seated in a chair.

In embodiments according to the invention, an immobilization device 320 is placed next to and against the patient 304 on the patient support device 308 during radiation therapy. The placement of the immobilization device 320 and the shape and relative size of the device shown in the example of FIG. 3 are examples only. In embodiments, the immobilization device 320 is worn by the patient 304. The immobilization device 320 can be custom-designed to fit the contours of the body of the patient 304. In general, the immobilization device 320 is a patient-specific device. That is, the immobilization device 320 is designed for and used by a single patient.

The immobilization device 320 helps to establish a fixed, defined location for the patient 304 on the patient support device 308 and also helps to establish a position (e.g., posture) for the patient. An immobilization device also helps to maintain the patient in the established location and position during the course of a radiation treatment session and to re-establish and maintain the patient's location and position in subsequent treatment sessions. In embodiments according to the invention, the immobilization device 320 has a shape that provides these functionalities. Such shapes are known in the art.

Conventionally, an immobilization device is placed so that it does not obstruct the path of the beam. In contrast, in embodiments according to the invention, the immobilization device 320 is placed in the beam path, between the nozzle 306 and a target in the patient 304, so that the beam passes through the immobilization device on its way to the target.

Thus, in embodiments, another purpose of the immobilization device 320 is to ensure that any path of a radiation beam from the nozzle 306 to a target inside the patient 304 will travel through substantially the same effective thickness of matter. That is, depending on the shape of the patient's body, the location of the target in the patient, and the shape of the target, a beam may pass through different amounts (depths) of tissue if those variables are not compensated for. Similarly, two or more beams that have parallel paths may each pass through different amounts of tissue. The shape of the immobilization device 320 can be designed to compensate for these types of differences. Thus, for beams such as proton beams, electron beams, neutron beams, photon beams, ion beams, and atomic nuclei beams, a uniform (or nearly uniform) dose can be delivered across the length (depth) of the target using a beam or beams that pass through the immobilization device 320.

Also, for proton beams and ion beams, the immobilization device 320 can be designed to locate the Bragg peak of the beam inside the target. Specifically, the Bragg peak can be located at the distal portion or edge of the target, and then moved along the beam path toward the proximal edge of the target by changing the beam energy to achieve a Spread Out Bragg Peak (SOBP). Also, as will be described (see FIG. 5A), the shape of the immobilization device 320 can be designed to achieve an SOBP.

The immobilization device 320 of FIG. 3 can be advantageously utilized with FLASH RT, although the invention is not so limited. In general, because of the higher dose rates associated with FLASH RT as mentioned above, it is desirable to minimize the amount of time that normal, healthy tissue outside the target is irradiated. A means of achieving that is to produce a radiation treatment plan in which beams do not overlap, or overlap as little as possible, outside the target. Another means of achieving that is to specify, during radiation treatment planning, limits for a maximum irradiation time and a minimum dose rate for normal, healthy tissue outside the target. However, it is still necessary to deliver the prescribed dose into and uniformly across the target. Immobilization devices in embodiments according to the invention can provide a uniform dose into and across a target and thus can facilitate radiation treatment planning using FLASH RT by resolving or contributing to the resolution of that aspect of the planning.

Figure 4:
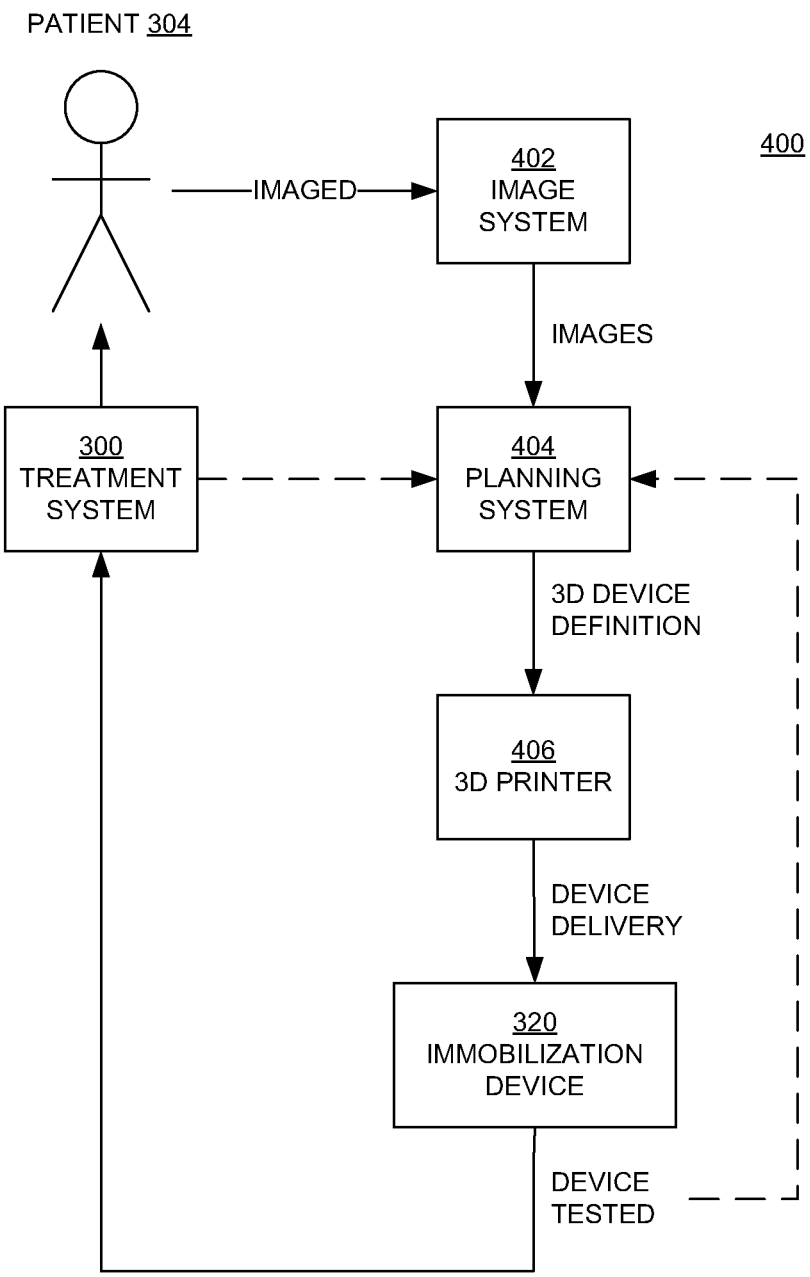
FIG. 4 is a block diagram illustrating components in a process for creating immobilization devices in embodiments according to the present invention.

As mentioned above, immobilization devices can be created by 3D-printing using a 3D printer. FIG. 4 is a block diagram illustrating components in a process 400 for creating immobilization devices in embodiments according to the present invention.

In the example of FIG. 4, a patient (e.g., the patient 304) is imaged using an image system 402 that uses, for example, x-rays, magnetic resonance imaging (MRI), and computed tomography (CT). When CT or MRI imagery, for example, is used, a series of two-dimensional (2D) images are taken from a 3D volume. Each 2D image is an image of a cross-sectional "slice" of the 3D volume. The resulting collection of 2D cross-sectional slices can be combined to create a 3D model or reconstruction of the patient's anatomy (e.g., internal organs). The 3D model will contain organs of interest, which may be referred to as structures of interest. Those organs of interest include the organ targeted for radiation therapy (a target), as well as other organs that may be at risk of radiation exposure during treatment.

One purpose of the 3D model is the preparation of a radiation treatment plan. To develop a patient-specific radiation treatment plan, information is extracted from the 3D model to determine parameters such as organ shape, organ volume, tumor shape, tumor location in the organ, and the position or orientation of several other structures of interest as they relate to the affected organ and any tumor. The radiation treatment plan can specify, for example, how many radiation beams to use and which angle each of the beams will be delivered from.

In embodiments according to the present invention, the images from the image system 402 are input to a planning system 404. In embodiments, the planning system 404 includes a computing system having a processor, memory, an input device (e.g., a keyboard), and a display. The system 100 of FIG. 1 is an example of a platform for the planning system 404.

Continuing with reference to FIG. 4, the planning system 404 executes software that is capable of producing printing plans for an immobilization device or devices customized to the patient 304 and to the treatment plan devised for the patient. The software may itself translate the output of the image system 402 (e.g., the 3D model) into files that can be used by the 3D printer 406. Alternatively, software may be used by a designer to produce such files based on the output of the image system 402 and also based on the treatment plan. The printing plans may be a design for an immobilization device, or it may be a design for a mold that can be used to fabricate the immobilization device. The planning system 404 outputs the files to the 3D printer 406, which produces the immobilization device(s) and/or mold(s).

The immobilization device 320 can be produced by the 3D printer 406 using a range of different materials suitable for such a device; that is, using materials that have the necessary radiological properties. If the 3D printer 406 is not capable of using such materials, then it can instead produce a mold that can be used to produce an immobilization device made of suitable materials. The immobilization device 320 can be 3D-printed as a single piece, or it can be 3D-printed as multiple pieces that are subsequently assembled.

The immobilization device 320 so produced can be inspected and tested as part of a quality assurance plan before the device is used with a patient. If the immobilization device 320 is deficient in some aspect, the printing plans can be adjusted to correct the deficiency before the immobilization device is used.

Some or all of the process 400 can be implemented on-site (e.g., at the treatment center). Accordingly, patient-specific devices can be readily, quickly, inexpensively, and effectively produced on-site without an external manufacturer, avoiding shipping from and perhaps back to the manufacturer. The number of patient visits can be reduced because, for example, the immobilization device can be fabricated when the patient arrives for a treatment and/or because the immobilization device can be quickly modified on-site after testing for fit and/or function or while the radiation therapy is being performed. Furthermore, the immobilization devices can be recycled and do not need to be stored.

Figure 5A:
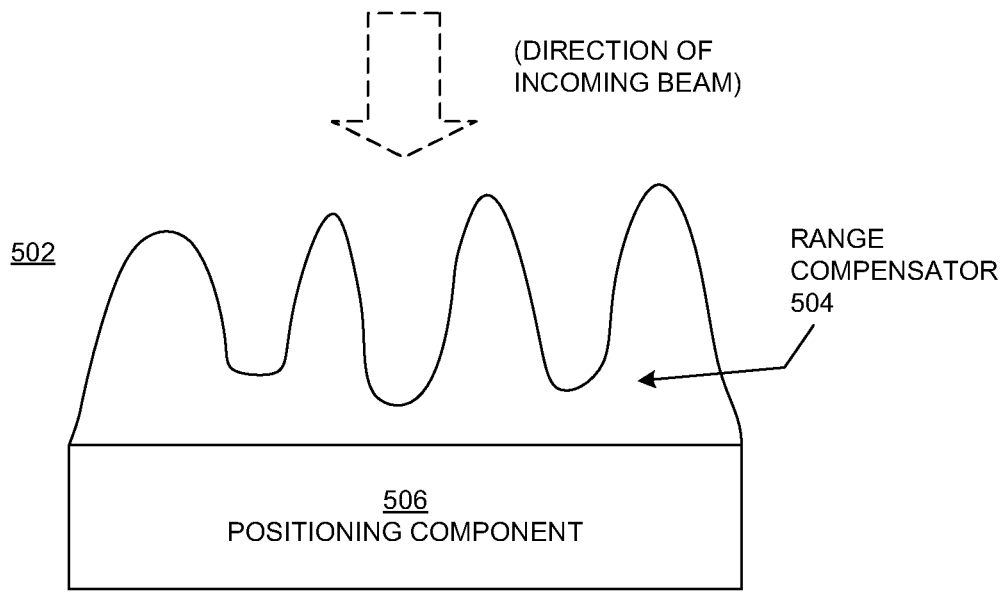
FIGS. 5A, 5B, 5C, and 5D illustrate immobilization devices in embodiments according to the present invention.

FIG. 5A illustrates an immobilization device 502 that can be 3D-printed in embodiments according to the present invention. The immobilization device 502 is an example of the immobilization device 320 of FIG. 3. The immobilization device 502 includes a range compensator 504 and a positioning component 506. The immobilization device 502 in general, and the range compensator 504 and positioning component 506 in particular, can be made of any suitable material or combination of materials including metal or plastic.

As discussed above, the immobilization device 502 is a patient-specific device designed or configured to hold a patient in place. The immobilization device 502 can also be designed or configured to compensate for differences in the amount of tissue that different beams may travel through, to provide a uniform dose across a target in the patient. In addition, in embodiments, the immobilization device 502 (specifically, the range compensator 504) is designed or configured to shape the distribution of the dose delivered to a patient. In embodiments, the treatment beam is a proton beam or an ion beam and the range compensator 504 is configured to locate the Bragg peak of the beam inside the target in the patient. In one such embodiment, the range compensator 504 is configured to locate the Bragg peak at the distal portion or edge of the target.

The shape of the range compensator 504 can be designed so that the Bragg peak of a proton beam or an ion beam can be moved within the target by directing the beam through different parts of the range compensator. For example, as shown in the example of FIG. 5A, the range compensator 504 has a non-uniform surface facing the incoming beam. Thus, the thickness of the range compensator 504 (where thickness is measured in the direction of the beam path) is not uniform. Consequently, by aiming the beam at one part of the range compensator 504, then another, and so on, the location of the Bragg peak in the target can be moved along the beam path between the distal and proximal portions of the target to create an SOBP. That is, different thicknesses of material can be placed in the path of the beam by aiming the beam at different parts of the range compensator 504, thus affecting the energies of the particles in the beam, thereby affecting the distance the particles penetrate into the target and the moving the location of the Bragg peak in the target to create an SOBP. An SOBP can also be achieved by varying the energy of the incident beam using the accelerator and beam transport system 204 (FIG. 2).

Continuing with reference to FIG. 5A, the positioning component 506 holds the immobilization device 502 in place relative to the patient. That is, the positioning component 506 holds the immobilization device 502 on the patient in a manner such that, if the patient moves, then the immobilization device also moves so that it is in the same location on the patient.

Figure 5B:
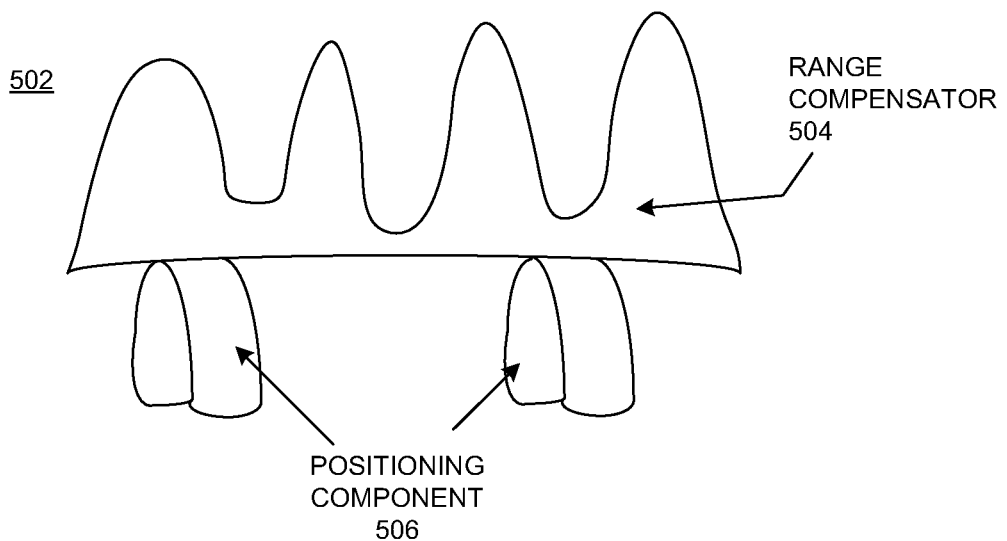

In embodiments, the positioning component 506 fastens the immobilization device 502 to the patient. For example, as shown in FIG. 5B, the positioning component 506 may consist of or include straps that can be extended around the patient (not shown) to hold the immobilization device 502 (specifically, the range compensator 504) in place against the patient. The surface of the immobilization device 502 that faces the patient can be contoured to match the contours of the patient's body.

Figure 5C:
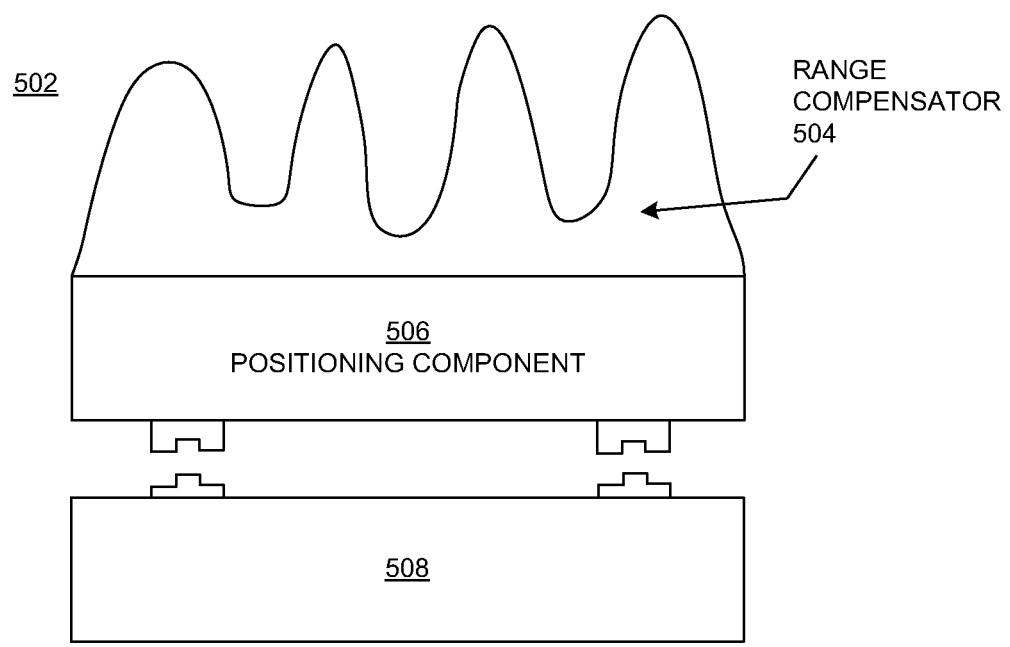

In another embodiment, with reference to FIG. 5C, the positioning component 506 attaches to an item 508 worn by the patient (not shown). For example, the patient may wear a garment that includes fasteners (e.g., snaps or VELCRO®) that mate with corresponding fasteners of the positioning component 506 to hold the immobilization device 502 (specifically, the range compensator 504) in place.

Figure 5D:
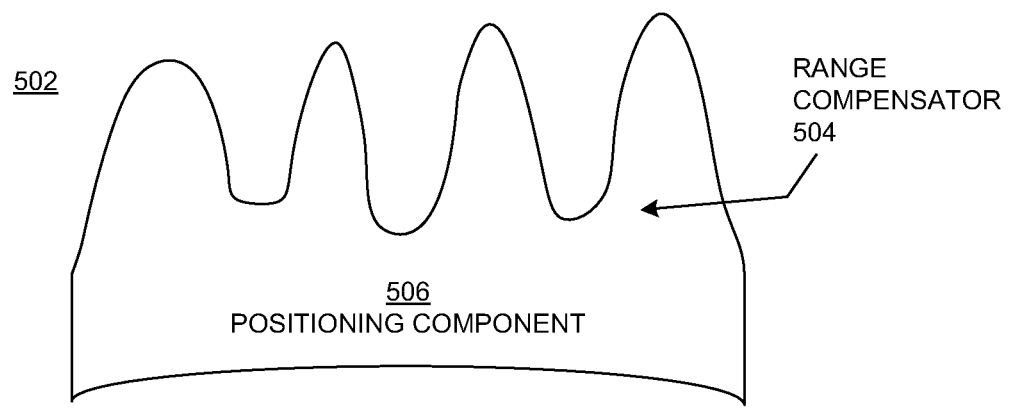

In embodiments, with reference to FIG. 5D, the range compensator 504 and the positioning component 506 are fabricated as a single piece.

Figure 6:
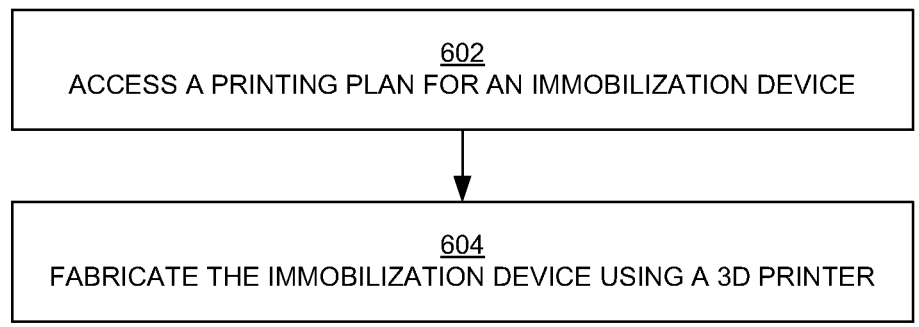
FIG. 6 is a flowchart of an example of computer-implemented operations for producing an immobilization device in embodiments according to the present invention.

FIG. 6 is a flowchart 600 of an example of computer-implemented operations for producing an immobilization device for limiting movement of a patient on a patient support device during radiation therapy in embodiments according to the present invention. The flowchart 600 can be implemented as computer-executable instructions residing on some form of computer-readable storage medium (e.g., using the computing system 100 of FIG. 1).

In block 602 of FIG. 6, a printing plan for an immobilization device is accessed from a memory of the computing system. The immobilization device includes features such as those described above in conjunction with FIGS. 3 and 5A-5D. Additional information is provided with reference to FIG. 4.

In block 604 of FIG. 6, a 3D printer is controlled using the printing plan to fabricate the immobilization device. Additional information is provided with reference to FIG. 4.

Figure 7:
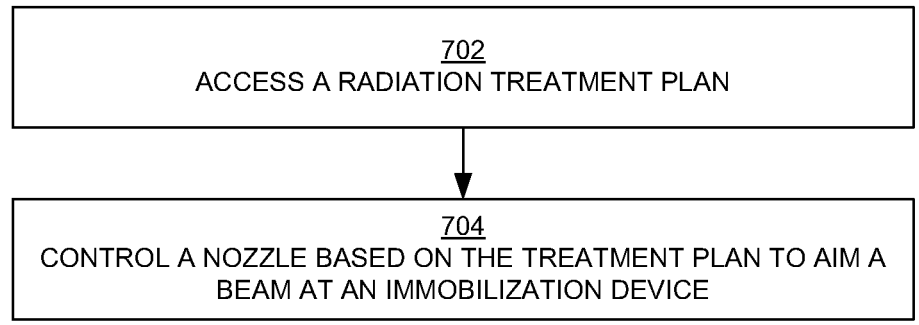
FIG. 7 is a flowchart of an example of computer-implemented operations for performing radiation treatment in embodiments according to the present invention.

FIG. 7 is a flowchart 700 of an example of computer-implemented operations for performing radiation treatment in embodiments according to the present invention. The flowchart 700 can be implemented as computer-executable instructions residing on some form of computer-readable storage medium (e.g., using the computing system 100 of FIG. 1).

In block 702 of FIG. 7, a radiation treatment plan is accessed from a memory of the computing system. The radiation treatment plan prescribes the dose or dose distribution to be delivered to a target in a patient by an incident beam emitted from a nozzle of a radiation treatment system.

In embodiments according to the invention, dose threshold curves are used to specify limits for the radiation treatment plan. A dose threshold curve provides a normal (healthy) tissue sparing-dose as a function of dose rate or irradiation time. The dose threshold curves can be tissue-dependent. For instance, the dose threshold curve for the lungs may be different from that for the brain. The appropriate dose threshold curve(s) can be to establish dose limits for radiation treatment planning. For example, the appropriate (e.g., tissue-dependent) dose threshold curve can be used to determine beam directions (gantry angles).

Dose limits can include, but are not limited to: a limit on irradiation time for each sub-volume (voxel) in the target (e.g., for each voxel of target tissue, treatment time less than x1 seconds); a limit on irradiation time for each sub-volume (voxel) outside the target (e.g., for each voxel of normal tissue, treatment time less than x2 seconds; x1 and x2 may be the same or different); a limit on dose rate for each sub-volume (voxel) in the target (e.g., for each voxel of target tissue, dose rate greater than y1 Gy/sec); and a limit on dose rate for each sub-volume (voxel) outside the target (e.g., f or each voxel of normal tissue, dose rate greater than y2 Gy/sec; y1 and y2 may be the same or different). In general, the limits are intended to minimize the amount of time that normal tissue is irradiated.

In block 704, the nozzle is controlled according to the treatment plan to aim the beam at an immobilization device like that of FIGS. 3 and 5A-5D.

In summary, embodiments according to the invention provide an improved immobilization device that is multifunctional. In addition to immobilizing a patient, the device can be used to shape the dose distribution within a target in the patient. In embodiments, the immobilization device includes a range compensator. In effect, in embodiments, the range compensator is moved from the nozzle of a radiation treatment system to the immobilization device. The multifunctional aspect of the immobilization device can improve radiation treatments and reduce costs. The immobilization device can be 3D-printed, which provides a number of benefits as well as explained above.

Range Compensators Positioned on a Patient for Radiation Therapy

Figure 8A:
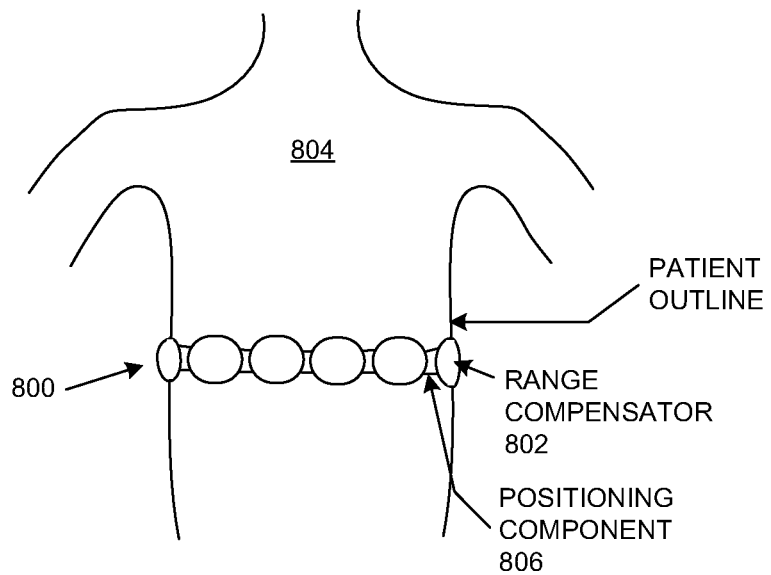
FIG. 8A is a system for treating a patient during radiation therapy in embodiments according to the present invention.

FIG. 8A is a system 800 for treating a patient 804 during radiation therapy in embodiments according to the present invention. The system 800 includes one or more range compensators (exemplified by the range compensator 802) and one or more positioning components (exemplified by the positioning component 806). In practice, each range compensator is located on the patient 804. The positioning component 806 holds the range compensator 802 in place relative to the patient 804 such that the range compensator lies on a path of a beam emitted from a nozzle of a radiation treatment system during radiation therapy.

Each of the range compensators shapes a distribution of a dose delivered to the patient 804 by the beam. The dose distribution may be relatively uniform across the target, or it may be non-uniform (e.g., the distribution may include a Bragg peak). Each range compensator can produce a different dose distribution in the target. In effect, the range compensator that conventionally is in, for example, the nozzle of a radiation treatment system is moved to locations on the patient 804. The range compensators described in conjunction with FIGS. 5A, 5B, 5C, and 5D are examples of the range compensator 802. One or more of the range compensators and one or more of the positioning components can be parts of an immobilization device as previously described herein. The range compensators and positioning components can be 3D-printed as previously described herein.

In embodiments, all of the range compensators are held in place on the patient 804 with a single positioning component. For example, the positioning component may be a belt worn by the patient 804, and each of the range compensators could be fastened to the belt. In another embodiment, the range compensators are held in place individually by a respective positioning component as described in conjunction with FIGS. 5A, 5B, 5C, and 5D.

In operation, the nozzle is aimed at a first one of the range compensators and the beam is turned on, delivering a distributed dose to the target along the beam path. That is, the path of the beam passes through the first range compensator, which affects the beam to produce a particular dose distribution in the target according to the design of the first range compensator. The first range compensator may have a non-uniform surface facing the beam as described above. In that case, the beam can be scanned across the surface of the range compensator to change the shape of the dose distribution within the target. The nozzle can be aimed at the first range compensator by moving the nozzle or by moving the patient 804 or by doing both (the patient is moved by moving the patient support device 208 of FIG. 2). After the beam is turned on for the time period specified by the radiation treatment plan (see, for example, the discussion of FIG. 7), the beam is turned off. The nozzle is then aimed at a second one of the range compensators (by moving the patient or the nozzle or both) and the beam is turned on again. Thus, the path of the beam now passes through the second range compensator, which affects the beam to produce a particular dose distribution in the target according to the design of the second range compensator. Like the first range compensator, the second range compensator can have a non-uniform surface facing the incoming beam and the beam can be scanned across the surface of the second range compensator. The energy or intensity of the beam transmitted through the second range compensator can be different from that transmitted through the first range compensator. The beam is turned off again after the time period specified by the radiation treatment plan. This process can be repeated for each of the range compensators. In this manner, different beam geometries are readily accommodated.

Figure 8B:
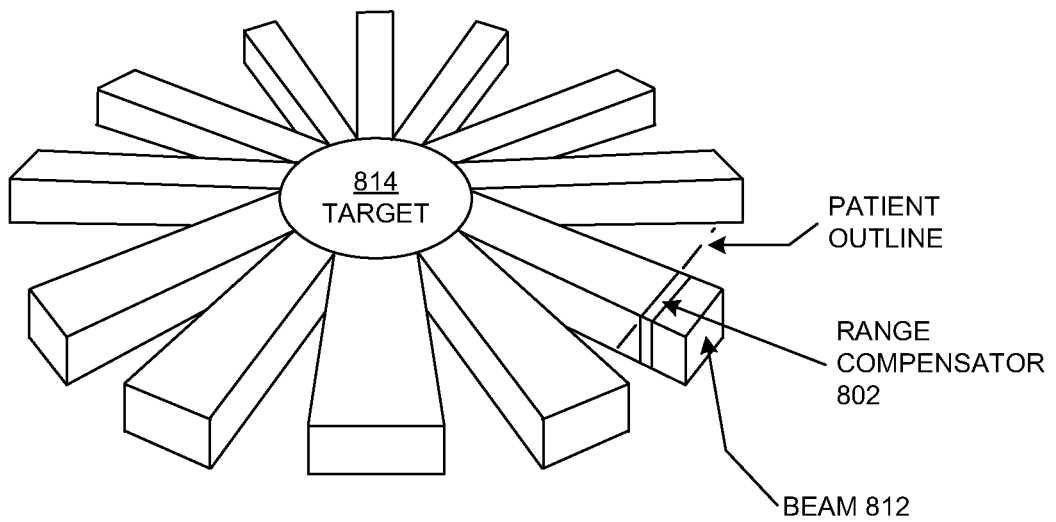
FIG. 8B illustrates a perspective view of an example of a beam geometry in embodiments according to the invention.

FIG. 8B is a perspective view of an example of a beam geometry in embodiments according to the invention. In the example of FIG. 8B, the beams (exemplified by beam 812) are in the same plane. The beams originate from a nozzle (not shown). Each beam can deliver a relatively high dose in a relatively short period of time. For example, each beam can deliver at least 4 Gy in less than one second, and may deliver as much as 20 Gy or 50 Gy or more in less than one second. In this example, the beams' paths overlap only within the target 814, and do not overlap outside the target in the surrounding tissue; however, the present invention is not so limited.

FIG. 8B shows the range compensator 802 in the path of the beam 812. The shape of the beam 812 and the shape of the range compensator 802 shown in the figure are for illustration purposes only. In general, the range compensator 802 is located on the outside of the patient (referred to as the patient outline), either on the patient's skin or on an article of clothing or the like worn by the patient. The beam 812 is aimed so that it passes through the range compensator 802. The other beams shown in the figure can pass through other range compensators (not shown).

Although all beams are shown in FIG. 8B, this does not mean that all beams are necessarily delivered at the same time or in overlapping time periods, although they can be. The number of beams delivered at any one time depends on the number of gantries or nozzles in the radiation treatment system and on the treatment plan.

Figure 8C:
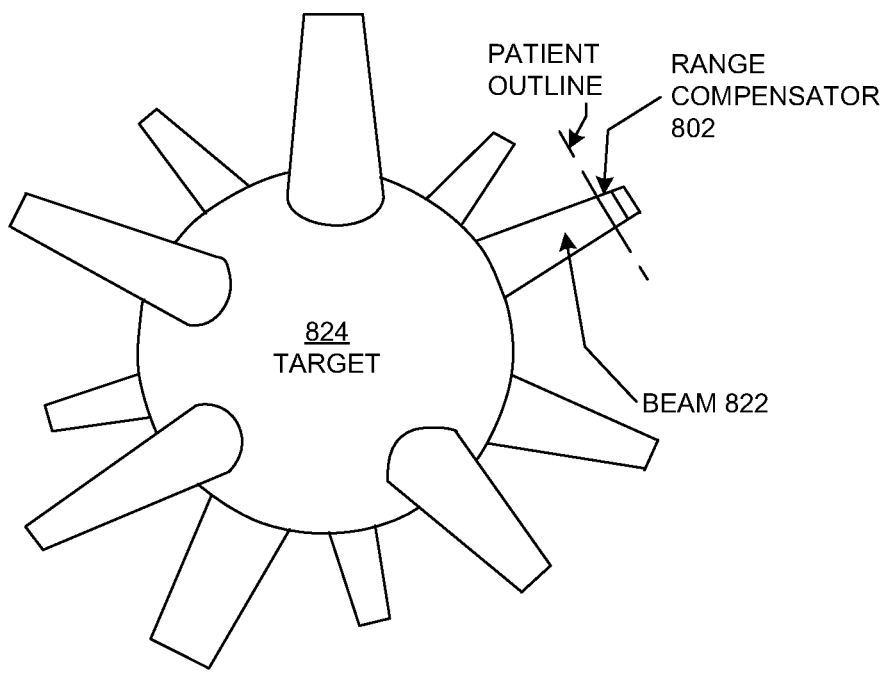
FIG. 8C illustrates a perspective view of an example of a beam geometry in embodiments according to the invention.

FIG. 8C illustrates a perspective view of an example of a beam geometry in embodiments according to the invention. In the example of FIG. 8C, the beams (exemplified by beam 822) are in different planes. In this example, the beams' paths overlap only within the target 824, and do not overlap outside the target in the surrounding tissue; however, the present invention is not so limited. Although all beams are shown in the figure, all beams are not necessarily delivered at the same time or in overlapping time periods as mentioned above.

FIG. 8C shows the range compensator 802 in the path of the beam 822. The shape of the beam 822 and the shape of the range compensator 802 shown in the figure are for illustration purposes only. In general, the range compensator 802 is located on the outside of the patient (the patient outline) as described above. The beam 822 is aimed so that it passes through the range compensator 802. The other beams shown in the figure can pass through other range compensators (not shown).

Thus, in embodiments according to the invention, range compensators are placed at locations on the patient 804 such that each of the beams shown in FIGS. 8B and 8C passes through a respective range compensator. In general, the surface of a patient can be viewed as having a number of discrete facets through which a beam may pass. From this perspective, for beams other than photon beams, each incident beam is orthogonal to a facet. In embodiments according to the invention, a range compensator can be located on each facet.

Figure 9:
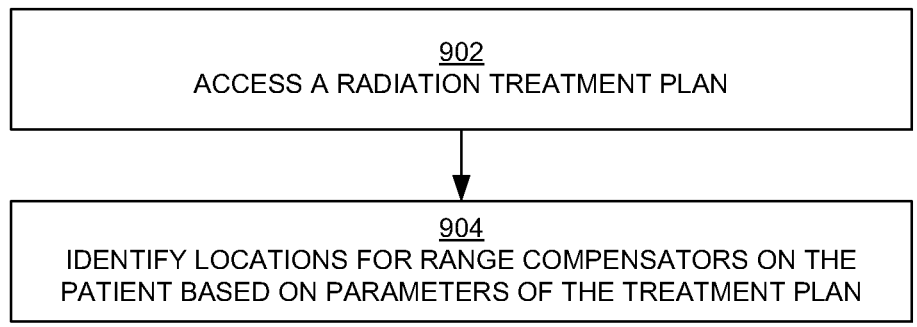
FIG. 9 is a flowchart of an example of computer-implemented operations for radiation treatment planning in embodiments according to the present invention.

FIG. 9 is a flowchart 900 of an example of computer-implemented operations for radiation treatment planning in embodiments according to the present invention. The flowchart 900 can be implemented as computer-executable instructions residing on some form of computer-readable storage medium (e.g., using the computing system 100 of FIG. 1).

In block 902 of FIG. 9, parameters for a radiation treatment plan are accessed from memory of the computing system. The parameters include, for example, the number of beams and paths of the beams relative to a position of a patient on a patient support device.

In block 904, locations on the patient for range compensators are identified. Each range compensator is strategically located on the patient so that each range compensator lies on at least one of the beam paths. Each range compensator shapes a distribution of a dose to be delivered to the patient by at least one of the beams.

Figure 10:
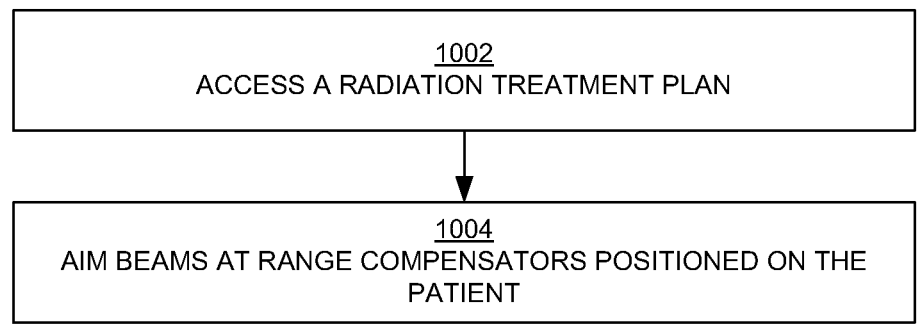
FIG. 10 is a flowchart of an example of computer-implemented operations for radiation treatment in embodiments according to the present invention.

FIG. 10 is a flowchart 1000 of an example of computer-implemented operations for radiation treatment in embodiments according to the present invention. The flowchart 1000 can be implemented as computer-executable instructions residing on some form of computer-readable storage medium (e.g., using the computing system 100 of FIG. 1 to implement the control system 210 of FIG. 2).

In block 1002 of FIG. 10, a radiation treatment plan is accessed from memory of the computing system. The radiation treatment plan prescribes a distribution of a dose to be delivered to a target in a patient by a number of beams emitted from a nozzle of a radiation treatment system.

In block 1004, the nozzle is controlled to aim the beams at range compensators positioned at different locations on the patient. Each range compensator shapes a distribution of a dose delivered to the patient by a respective beam. The nozzle is aimed at a first range compensator, and then a first beam is turned on and emitted at the first range compensator. The first beam is then turned off, the nozzle is aimed at a second range compensator, and a second beam is turned on and emitted at the second range compensator. This process can be repeated for each of the number of beams.

In summary, range compensators in embodiments according to the invention can be used to shape dose distribution in the target in lieu of, but also in combination with, a conventional range compensator. By strategically locating the range compensators on the patient, different beam geometries are readily accommodated. For radiation therapy including FLASH RT, it is not necessary to wait until a range compensator is adjusted when the beam geometry changes; instead, a properly configured range compensator is already in place. Thus, radiation therapy including FLASH RT can be quickly performed, thereby facilitating patient comfort. Range compensators in embodiments according to the invention also can be used to provide the prescribed dose inside the target and thus can facilitate radiation treatment planning using FLASH RT by making it easier to address that aspect of the planning.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for treating a patient during radiation therapy, the system comprising:
   multiple range compensators; and
   a single positioning component coupled to the multiple range compensators, wherein each range compensator of the multiple range compensators respectively shapes a distribution of a dose delivered to the patient by a respective beam of a plurality of beams emitted from a nozzle of a radiation treatment system along different paths between the nozzle and a target in the patient, and wherein the multiple range compensators are located on the single positioning component to hold the multiple range compensators in place on the patient at respective locations corresponding to the different paths.

2. The system of claim 1, wherein said each range compensator has a non-uniform thickness measured in the direction of the respective path of the respective beam.

3. The system of claim 1, wherein the plurality of beams comprises beams selected from the group consisting of proton beams and ion beams, and wherein said each range compensator is configured to locate a Bragg peak of the respective beam inside the target in the patient.

4. The system of claim 1, wherein the multiple range compensators are part of an immobilization device that limits movement of the patient on a patient support device relative to the beams.

5. The system of claim 4, wherein the single positioning component fastens the immobilization device to the patient.

6. The system of claim 4, wherein the single positioning component fastens the immobilization device to an item worn by the patient.

7. The system of claim 1, wherein the single positioning component has a shape that fits contours of the patient.

8. The system of claim 1, wherein the multiple range compensators and the single positioning component are fabricated as a single piece.

9. The system of claim 1, wherein the radiation treatment system is coupled to a treatment planning system comprising a computing system having a processor and memory, wherein the treatment planning system is coupled to a three-dimensional printer.

10. The system of claim 9, wherein the treatment planning system further comprises an image system operable for imaging the patient.

11. The system of claim 1, wherein each beam of the plurality of beams delivers a dose rate of at least four grays in less than one second.

* * * * *